US009011765B2

(12) United States Patent
Rahn et al.

(10) Patent No.: US 9,011,765 B2
(45) Date of Patent: Apr. 21, 2015

(54) METHOD AND ARRANGEMENT FOR STERILIZATION, IN PARTICULAR FOR THE STERILIZATION OF AN ADSORBER

(75) Inventors: Holger Rahn, Wendel (DE); Hans-Peter Leinenbach, Krems (AT); Stefan Kuhn, Neunkirchen (DE); Franz-Josef Gerner, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1007 days.

(21) Appl. No.: 13/125,344

(22) PCT Filed: Oct. 22, 2009

(86) PCT No.: PCT/EP2009/007565
§ 371 (c)(1),
(2), (4) Date: Jul. 8, 2011

(87) PCT Pub. No.: WO2010/046107
PCT Pub. Date: Apr. 29, 2010

(65) Prior Publication Data
US 2011/0262300 A1 Oct. 27, 2011

(30) Foreign Application Priority Data

Oct. 24, 2008 (DE) .......................... 10 2008 053 131

(51) Int. Cl.
*A61L 2/08* (2006.01)
*A61L 2/00* (2006.01)
*A61M 1/16* (2006.01)

(52) U.S. Cl.
CPC ............... *A61L 2/007* (2013.01); *A61L 2/0035* (2013.01); *A61L 2/08* (2013.01); *A61L 2202/122* (2013.01); *A61M 1/168* (2013.01)

(58) Field of Classification Search
CPC .............. A61K 41/00; A61K 41/0009; A61K 41/0019; A61L 2/00; A61L 2/0005; A61L 2/0011; A61L 2/0029; A61L 2/0035–2/0058; A61L 2/26; A61L 2202/00; A61L 2202/20; A61L 2202/22
USPC ........................................ 422/22, 24; 206/438
See application file for complete search history.

(56) References Cited

U.S. PATENT DOCUMENTS 4,880,548 A * 11/1989 Pall et al. ...................... 210/767
5,186,826 A     2/1993 Otto et al.
(Continued)

FOREIGN PATENT DOCUMENTS

| CA | 2663443   | 3/2008 |
| DE | 298 01 590 | 4/1998 |

(Continued)

OTHER PUBLICATIONS

International Preliminary Report on Patentability for PCT/EP2009/007565 mailed on Apr. 26, 2011.
(Continued)

*Primary Examiner* — Sean E Conley
(74) *Attorney, Agent, or Firm* — Kenyon & Kenyon LLP (57) ABSTRACT

A method and an arrangement for sterilizing, in particular for sterilizing an adsorber, which has an adsorber housing that is to be filled with an adsorbent, are such that, instead of the adsorbent-filled adsorber housing being sterilized, the adsorbent is sterilized in a separate container, which is dimensioned such that the adsorbent spreads out in a thin layer in the container. Together with the adsorber housing, the container for sterilizing the adsorbent forms a closed system, such that the adsorbent can be transferred into the adsorber housing without the need for an aseptic environment. The container for receiving the adsorbent is preferably a bag, in which the adsorbent spreads out in a thin layer when the bag is lying flat on a plane surface. Since the adsorbent in the bag spreads out in a thin layer, the sterilization requires only a relatively small dose of radiation, which cannot damage the adsorbent. The bag is irradiated with high-energy radiation, in particular ionizing radiation. The adsorbent is then transferred from the bag into the adsorber housing. During the transfer of the adsorbent into the adsorber housing, the air and/or excess liquid present in the adsorber housing is removed from the adsorber housing preferably into one or more empty bags.

13 Claims, 4 Drawing Sheets

(56) References Cited

U.S. PATENT DOCUMENTS

| | | | |
|---|---|---|---|
| 5,839,258 A | 11/1998 | Takayanagi et al. | |
| 2004/0219056 A1 | 11/2004 | Tribelsky et al. | |
| 2005/0142542 A1 | 6/2005 | Hei et al. | |
| 2010/0133203 A1* | 6/2010 | Walker et al. | 210/748.11 |

FOREIGN PATENT DOCUMENTS

| | | |
|---|---|---|
| EP | 0 507 245 | 10/1992 |
| EP | 0 933 090 | 8/1999 |
| EP | 1 625 859 A1 | 2/2006 |
| EP | 1 902 740 | 3/2008 |
| WO | WO 02/38447 | 5/2002 |
| WO | WO 2006/015603 | 2/2006 |

OTHER PUBLICATIONS

PCT International Search Report for PCT/EP2009/007565 mailed on Feb. 16, 2010.

* cited by examiner

METHOD AND ARRANGEMENT FOR STERILIZATION, IN PARTICULAR FOR THE STERILIZATION OF AN ADSORBER

FIELD OF THE INVENTION

The present invention relates to a method and an arrangement for sterilization, in particular for the sterilization of an end-of-line pack and in particular of an adsorber which has an adsorber housing to be filled with an adsorbent.

BACKGROUND

Various treatment procedures are known which make use of an adsorber. Adsorber therapies are innovative treatment procedures which remove pathogenic substances from the patient's blood outside the body. LDL cholesterol, for example, can be removed from whole blood with LDL apherase. Immunoadsorption, for example, allows antibodies to be removed from the patient's blood.

Known adsorbers have an adsorber housing which is densely packed with an adsorbent. The adsorber housing is generally a hollow cylindrical housing which is closed off at the top and bottom ends. The housing has an inlet at the top end and an outlet at the bottom end. A screen arranged upstream of the outlet stops the adsorbent from escaping from the housing.

Sterilization of the adsorber housing filled with the adsorbent is performed by means of high-energy ionizing radiation, such as $\alpha$, $\beta$, or $\gamma$ radiation, with sterilization by $\beta$ radiation being preferred. However, if it is of too high an intensity this high-energy radiation may damage the adsorbent. It is therefore important for the intensity of the radiation to be sufficient for sterilization but for the radiation not to be of too high an energy, to prevent the adsorbent from being damaged. The intensity of $\beta$ radiation is reduced by absorption in the adsorbent, there being a considerable decrease in the intensity of the radiation as the beam path becomes increasingly long. The energy loss of the particle radiation first increases per wavelength unit during the path covered by the particles, then falls abruptly after a maximum. The energy loss per wavelength unit is described by the Bragg curve.

It is proving to be a disadvantage in practice that, due to their geometrical dimensions, the known adsorber housings require a relatively high intensity of radiation to ensure that the adsorbent is sterilized even in the innermost region of the housing. On account of an excessively high radiation intensity at a layer depth around the maximum of the Bragg curve, however, there is the risk of damage to at least a part of the absorbent. To date, this problem has been solved by drying the adsorbent, because the depth of penetration of ionizing $\beta$ radiation is greater in dry material than in wet material. However, this procedure calls for the additional step of drying in the procedure, which also involves the consumption of additional energy.

Known from United Kingdom Patent Publication No. 1 GB 655 198 is a method and an apparatus for the irradiation of thin films of liquid. The known apparatus comprises a rotating cylinder over the wall of which the liquid to be irradiated flows. The principle of the sterilization of thin layers by radiation is also known from PCT Publication No. WO 2007/075931 A1.

The above-mentioned problems arise not only in the sterilization of an adsorbent in an adsorber housing but also in the sterilization of other materials sensitive to radiation which are to be made available in a container, such for example as medications for infusion but also nutrients.

The object underlying the present invention is therefore to specify a simplified method of sterilization in which the risk of damage to the material to be sterilized, which may in particular be an adsorbent, does not exist.

A further object of the present invention is to provide an arrangement for sterilization by which sterilization is simplified without there being any risk of the material to be sterilized, which may in particular be an adsorbent, being damaged.

These objects are achieved in accordance with the present invention by virtue of the features of the embodiments of the present invention described herein.

SUMMARY

The method according to the present invention for the sterilization of a material which is to be made available in a container, is based on a separate containing means, which forms a closed system with the container in which the material is to be sterilized, being filled with the material to be sterilized, the separate containing means for sterilization being of a size such that the material to be sterilized distributes itself in the containing means in a thin film or layer. At least the separate containing means holding the material to be sterilized is then irradiated with high-energy radiation. It is preferably the entire closed system which is irradiated. Because the container in which the material is to be sterilized and the containing means for sterilization form a closed system, the material which has been sterilized can be transferred aseptically into the container in which the material is to be made available. This has the advantage that there is no need for any aseptic filling of the container in which the material is to be made available in a non-sterile environment. Sterilization by the method according to the present invention is thereby simplified.

The method according to the present invention and the arrangement according to the present invention have proved particularly advantageous for the sterilization of an adsorber which has an adsorber housing which is to be filled with an adsorbent. The method according to the present invention and the arrangement according to the present invention are based not on the adsorber housing filled with the adsorbent being sterilized but on the adsorbent being sterilized without the adsorber housing in a separate containing means which is of a size such that the adsorbent distributes itself in the containing means in a thin film or layer. What is meant in this case by a thin film or layer is a film or layer of a thickness of up to 30 mm, and preferably of a thickness of less than 20 mm and, as a particular preference, of a thickness of between 5 and 10 mm. What is suitable for this is any containing means which is of adequate dimensions in relation to the volume of the adsorbent. Even a shallow containing means whose height is very small in relation to its width and length is adequate.

Since the material to be sterilized in the containing means is distributed in a thin layer, the intensity of the radiation inside the thin layer changes only negligibly. On account of the uniform distribution of the intensity of the radiation, the material can be irradiated with an intensity of radiation which in principle is required for the sterilization at the surface. On the one hand, this ensures that the whole material is irradiated with an adequate intensity, and on the other hand there is no risk of damaging at least a part of the adsorbent due to an excessively high intensity of radiation in individual regions of the deeper layers.

The method according to the present invention can however also be used for all other materials which are sensitive to radiation, such for example as materials for infusion but also nutrients, which are to be made available in an end-of-line pack. These materials should be flowable or pourable to enable them to be transferred from the containing means for sterilization into the container in which they are to be made available.

In an embodiment which is a particular preference, the containing means for receiving the adsorbent is a bag in which the adsorbent distributes itself in a thin film or layer when the bag is lying flat on a plane. The bag is preferably a film bag produced from two films situated one above the other or from a tube of film. Bags of this kind for receiving medical liquids/fluids are generally familiar. A bag rather than a rigid container also has the advantage that the adsorbent may be transferred easily from a bag. As a result, the bag may be emptied easily and completely.

Because the adsorbent distributes itself in a thin layer in the containing means, the intensity of the radiation inside the thin layer varies only slightly. The containing means is irradiated with high-energy, and in particular ionizing, radiation, such for example as $\alpha$, $\beta$ or $\gamma$ radiation and preferably $\beta$ radiation. The adsorbent is then transferred from the containing means to the adsorber housing. It is possible for only the containing means holding the adsorbent to be irradiated. What is preferably irradiated, however, is the whole arrangement which comprises, as a closed system, the adsorber housing and the containing means for receiving the adsorbent.

When the adsorbent is transferred into the adsorber housing, the air and/or the excess liquid/fluid situated in the adsorber housing is preferably fed away out of the adsorber housing.

In a preferred embodiment, air and/or excess liquid/fluid is transferred into one or more separate containing means. However, when this is done it has to be ensured that the adsorber housing, the containing means for receiving the adsorbent, and any further containing means once again form a closed system. The containing means for receiving air and/or liquid/fluid, which is preferably once again a bag, is preferably connected to the adsorber housing via one or more flexible lines.

In an alternative embodiment, a closed system is created which has one or more sterile barriers, and in particular sterile membranes which are hydrophobic, i.e., which are permeable to air but not permeable to liquid/fluid, which seal off one or more venting openings in the adsorber housing in a sterile manner. It is, however, possible in this embodiment for the adsorber housing only to be vented of air but for excess liquid/fluid not to be fed away.

In another preferred embodiment, the air and/or excess liquid/fluid situated in the adsorber housing is not transferred into one or more separate containing means but into the container for receiving the adsorbent, which has been emptied.

For use to be made of the adsorber housing, the flexible lines are severed. The flexible lines may be closed off with shut-off devices of various designs. It is, however, also possible for the flexible lines to be welded shut sterilely. Basically, all known devices and methods by which the flexible lines can be severed or closed off sterilely are possibilities.

In an embodiment which is a particular preference, the air and/or the excess liquid/fluid situated in the adsorber housing is fed away at two opposite ends or sides of the adsorber housing, and preferably from what are the top and bottom ends of the adsorber housing when in the in-use position. The air and/or liquid/fluid may be transferred into one separate containing means or two separate containing means in this case. The containing means, which are preferably bags, may be separate bags or separate chambers of a multi-chambered bag. An embodiment which is a particular preference makes provision for the bag for receiving the adsorbent and the two bags for receiving air and/or liquid/fluid to form one multi-chambered bag, i.e. a three-chambered bag.

The containing means for receiving the adsorbent preferably has an inlet via which the containing means may be filled with the adsorbent. Connected to the inlet there may be a flexible line or a connector for connecting on a flexible line.

The containing means may be filled with a liquid/fluid material or a dry but pourable material, in particular an adsorbent. After the sterilization, the liquid/fluid material, and in particular the adsorbent, may be transferred into the container, and in particular the adsorber housing, as a suspension. The dry material, and in particular the dry material in powder form, may, after the sterilization, either be transferred in the dry state or may first be dissolved or suspended in a liquid/fluid and then transferred in the liquid/fluid state. The liquid/fluid may, once again, be made available in a containing means and in particular in a bag, Another embodiment which is a particular preference makes provision for flushing of the containing means for receiving the adsorbent. In this embodiment, the arrangement according to the present invention comprises a further containing means for receiving a flushing liquid/fluid, which flushing liquid/fluid is transferred into the emptied containing means for receiving the adsorbent once the adsorbent has been transferred into the adsorber housing. After the containing means has been flushed, the flushing liquid/fluid is then transferred into the adsorber housing together with the remainder of the adsorbent, with excess liquid/fluid and/or air once again being fed away out of the adsorber housing.

Various embodiments of the present invention are explained in detail below by reference to the drawings.

DETAILED DESCRIPTION

Figure 1:
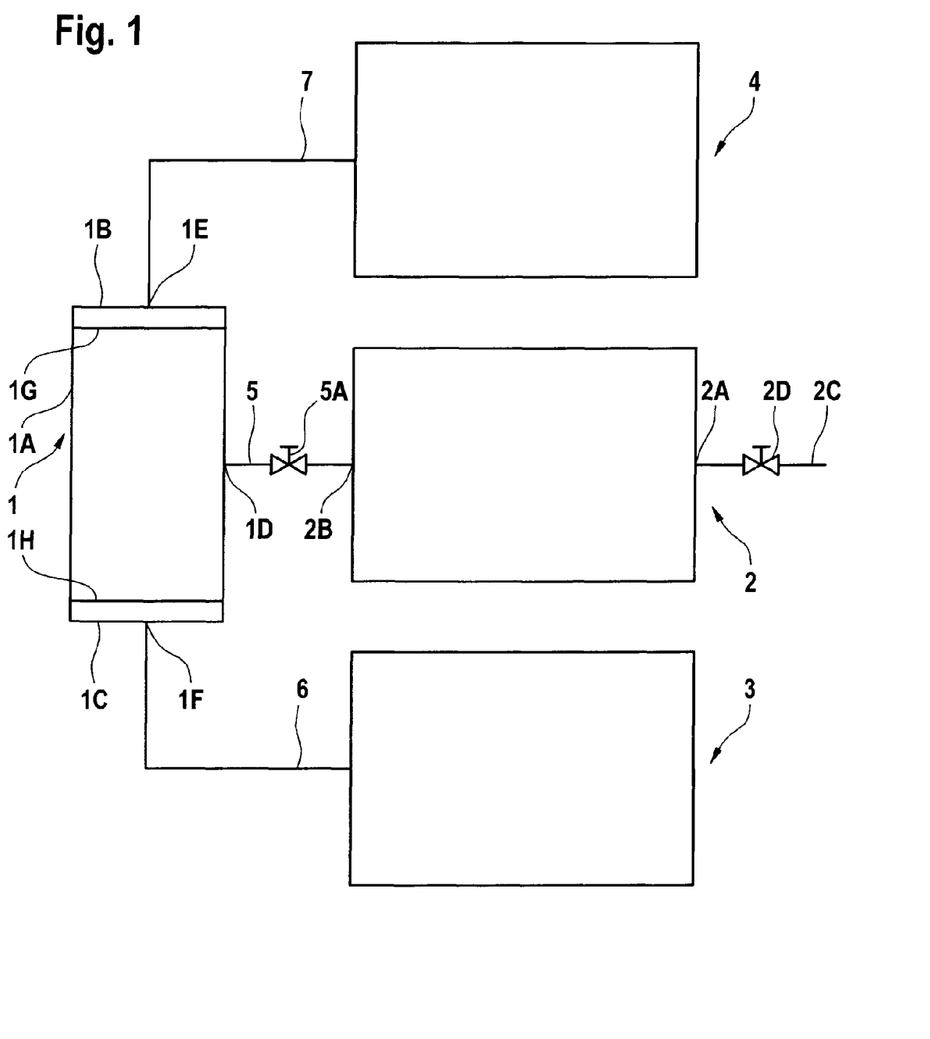
FIG. 1 is a highly simplified schematic view of a first embodiment of arrangement according to the present invention for the sterilization of an adsorbent, in which air and/or excess liquid/fluid situated in the adsorber housing is transferred into two empty bags.

FIG. 1 is a highly simplified schematic view of a first embodiment of arrangement according to the present invention for the sterilization of an adsorber. Rather than an adsorber, what may however also be sterilized by the method according to the present invention are any other end-of-line packs which have to be filled with materials which are sensitive to radiation.

The arrangement according to the present invention comprises the adsorber 1, a containing means 2 for receiving an adsorbent in the form of a suspension, and a first and a second containing means 3, 4 for receiving air and/or excess liquid/fluid which is situated in the adsorber housing. The containing means for receiving, respectively, an adsorbent and air and/or liquid/fluid are conventional bags which are in general use in medical technology. Bags of this kind are produced from two films situated one above the other which are welded together in the edge region by a surrounding weld. The bags may however also be produced from a tube of film which is welded together by welds at its ends. Because bags of this kind are part of the prior art, there is no need for any further description of them.

What is crucial for the purposes of the present invention is that the bag for receiving the adsorbent is of sufficient size in relation to the volume of the adsorbent. If the bag is lying flat on a plane, the adsorbent distributes itself in the bag in a thin layer or film.

The adsorber 1 is a conventional adsorber which is to be filled with the adsorbent. The adsorber has a hollow cylindrical adsorber housing 1A which is closed off at the ends by a cover part 1B and a floor part 1C. An adsorber of this kind is known from, for example, European Patent Publication No. EP 0 507 245 B1. Because the adsorber as such is part of the prior art, what will be described here are only the parts which are relevant to the present invention. For example, the inlet and outlet of the adsorber for feeding in the blood to be treated and feeding it away have not been shown.

The bag 2 for receiving the adsorbent has an inlet opening 2A for filling the bag 2 with an adsorbent in the form of a suspension, and an outlet opening 2B for emptying the bag. Running to the inlet opening 2A is a flexible line 2C which is closed off by a shut-off device 2D. Connected to the outlet opening 2B is one end of a flexible line 5 whose other end is connected to an inlet opening 1D in the adsorber housing 1A. A shut-off device 5A is provided for opening and closing the flexible line 5. Basically however, it is also possible for the bag 2 to be filled via the line 5 and for the bag to be connected to the adsorber housing after this. In this embodiment, the line 2 and the inlet opening 2A can be dispensed with.

The adsorber housing 1A has a top venting opening 1E in the cover part 1B and a bottom venting opening 1F in the floor part 1C. In the hollow cylindrical adsorber housing 1A, a top filtering screen 1G is arranged below the top venting opening 1E and a bottom filtering screen 1H is arranged above the bottom venting opening 1F, which filtering screens are intended to retain the adsorbent. The first bag 3 for receiving air and/or liquid/fluid is connected to the bottom venting opening 1F via a flexible line 6, and the second bag 4 for receiving air and/or liquid/fluid is connected to the top venting opening 1E via a flexible line 7.

Because it is only the principle that is important in the present case, for greater clarity the parts familiar to the person skilled in the art for connecting the flexible lines to the bags have not been shown.

In what follows, the method according to the present invention will be described by taking as an example the method of sterilizing an adsorber by using the arrangement according to the present invention.

The shut-off device 2D in or on the flexible line 2C for feeding in the adsorbent is first opened, and the adsorbent is conveyed from a reservoir (not shown), via the flexible line 2C, into the bag 2. When this is done, the bag 2 is lying flat on a plane, which means that the adsorbent distributes itself in the bag as a thin film. The shut-off device 2D is then closed.

The entire arrangement is then irradiated with ionizing radiation, such for example as $\alpha$, $\beta$ or $\gamma$ radiation and preferably $\beta$ radiation. It is, however, also possible for only the bag 2 holding the adsorbent to be irradiated. At this time, the intensity of the irradiation has to be adjusted in such a way that the intensity is suitable for the sterilization. Since the intensity of the radiation inside the thin layer in the bag scarcely changes, the intensity of the radiation does not need to be adjusted higher or lower than the intensity that is generally sufficient for the sterilization at the surface. The adsorber housing 1A can then be filled. After the sterilization, what exists is still a closed system because the individual containing means are still connected to the flexible lines. The adsorbent may thus be transferred, in the closed system, from the bag 2 into the adsorber housing 1A without the need for an aseptic environment. There is a guarantee of sterility when this is done.

After the irradiation, the shut-off device 5A on or in the flexible line 5 is opened. The adsorbent situated in the bag 2 is then transferred into the adsorber housing 1A. This may be done by arranging the bag 2 above the adsorber housing so that the suspension will flow into the adsorber housing by gravity. The bag 2 may however also be squeezed to transfer the suspension or the flexible line may be inserted in a flexible tube pump. This is advisable anyway to allow the bag to be completely emptied. Once the bag has been emptied, the shut-off device 5A is closed again.

When the adsorbent is being transferred, the air and excess liquid/fluid situated in the adsorber housing 1A flow out of the adsorber housing 1A and into the two empty bags 3, 4, via the flexible lines 6 and 7. The filtering screens 1G, 1H provided in the adsorber housing 1A stop any solid substances from making their way into the empty bags.

Once the adsorber housing has been completely filled with the adsorbent, the flexible lines 5, 6 and 7 are welded shut sterilely, and the adsorbent is thus cut off from the bags 2, 3, 4. It is however also possible for shut-off devices to be provided to shut off the flexible lines.

Figure 2:
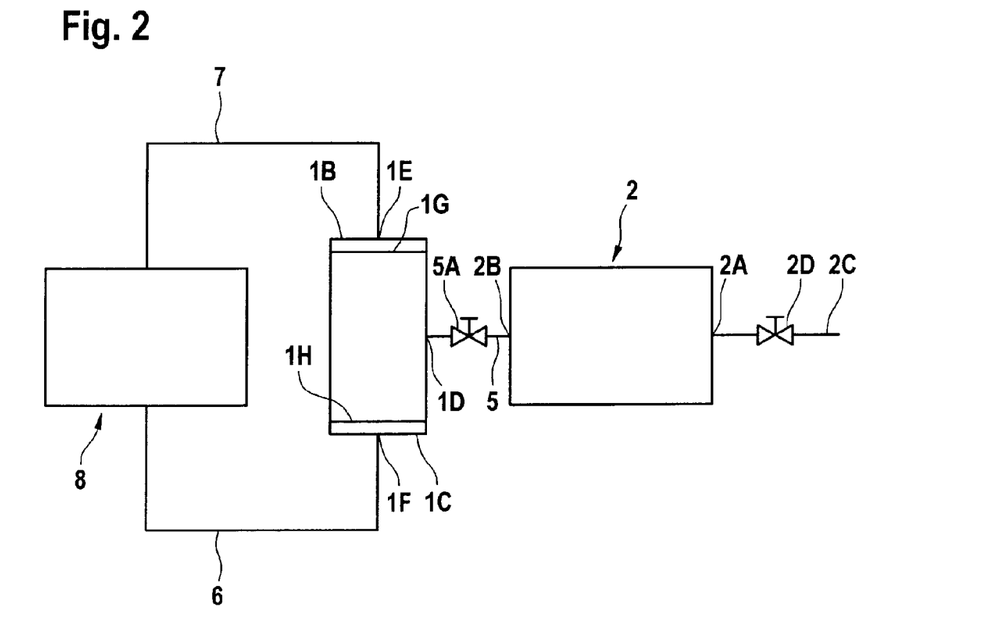
FIG. 2 shows a second embodiment of arrangement according to the present invention, in which air and/or excess liquid/fluid situated in the adsorber housing is transferred into one empty bag.

FIG. 2 shows an alternative embodiment of an arrangement according to the present invention which differs from the embodiment shown in FIG. 1 only in that only one empty bag 8 is provided for receiving air and/or liquid/fluid rather than two empty bags 3, 4. Items which correspond to one another have therefore been given the same reference numerals. In this embodiment, the two flexible lines 6, 7 are connected to opposite ends or sides of the single empty bag 8 from one another. In operation, the only difference between the two embodiments is that air and/or liquid/fluid flow from the adsorber housing 1A not into two but only into one empty bag 8.

Figure 3:
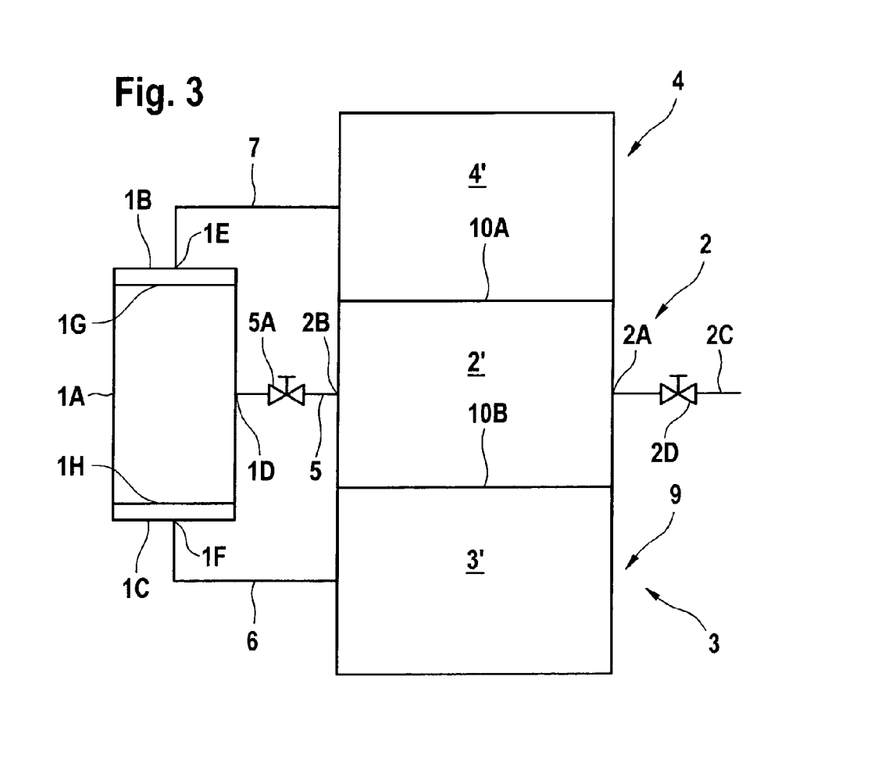
FIG. 3 shows a further embodiment of arrangement according to the present invention, in which the bag for receiving the adsorbent and the bags for receiving the air and/or liquid/fluid form one multi-chambered bag.

FIG. 3 shows another embodiment of arrangement according to the present invention, which differs from the embodiment shown in FIG. 1 only in that the bag 2 for receiving the adsorbent and the bags 3, 4 for receiving air and/or liquid/fluid are in the form of a multi-chambered bag 9. Items which correspond to one another have therefore been given the same reference numerals. The three-chambered bag 9 has one chamber 2' for the adsorbent and two chambers 3' and 4' for air and/or liquid/fluid. The three chambers 2', 3', 4' are separated from one another by transversely extending welds 10A, 10B. The three-chambered bag 9 simplifies handling in that all the bags 2, 3, 4 form a single unit.

Figure 4:
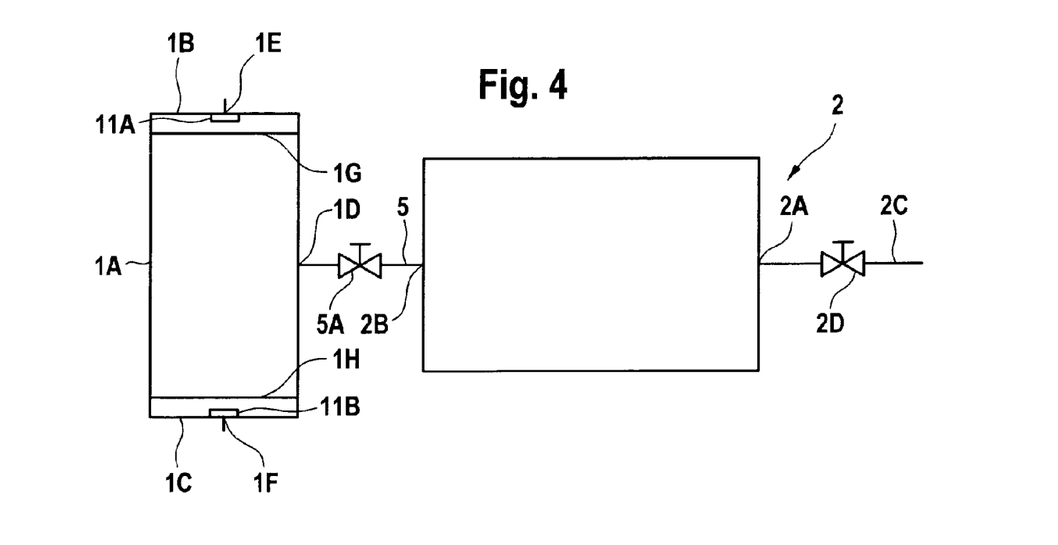
FIG. 4 shows a further embodiment of arrangement according to the present invention, in which air situated in the adsorber housing is fed away into the surroundings.

FIG. 4 shows another embodiment of arrangement according to the present invention which differs from the embodiment shown in FIG. 1 only in that the bags for receiving air and/or liquid/fluid are not present. Items which correspond to one another have once again been given the same reference numerals. In this embodiment, the top and bottom venting lines 1E and 1F of the adsorber housing 1A are closed off by sterile barriers, such for example as by sterile membranes 11A, 11B which are hydrophobic, i.e., which are permeable to air but not permeable to liquid/fluid, which sterile membranes are only indicated. When the adsorber housing is being filled, air can escape through the membranes but the liquid/fluid is held back. Hence excess liquid/fluid cannot be fed away in this embodiment. Otherwise, the embodiment shown in FIG. 4 is operated in the same way as the embodiment shown in FIG. 1.

Figure 5:
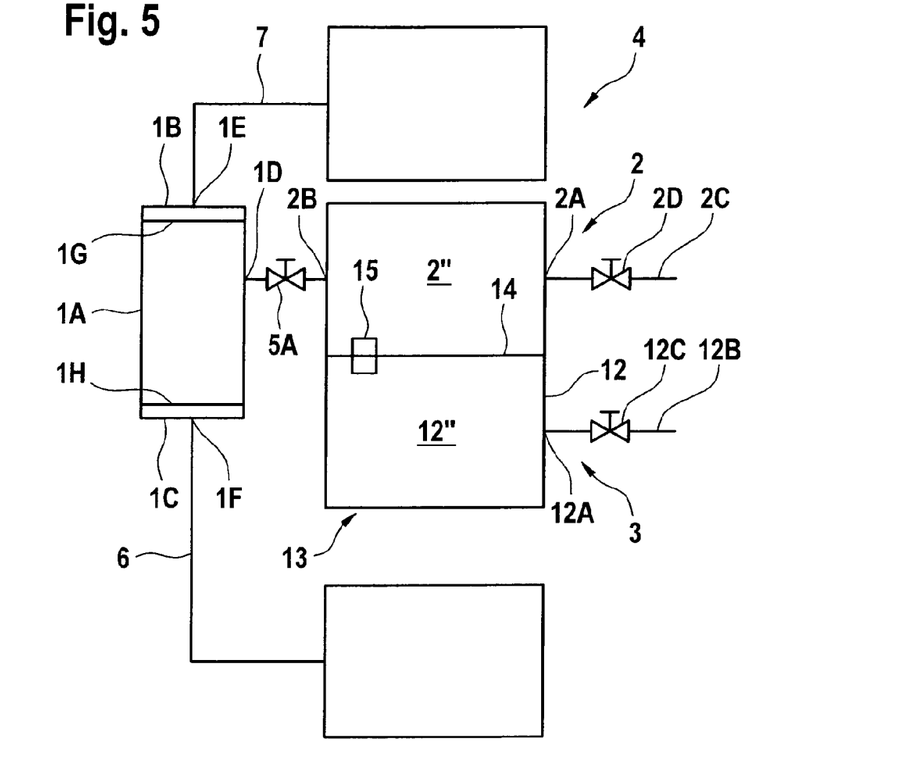
FIG. 5 shows a further embodiment of arrangement according to the present invention, in which flushing of the bag for receiving the adsorbent is permitted.

FIG. 5 shows another embodiment of arrangement according to the present invention which differs from the embodiment shown in FIG. 1 in that the arrangement comprises an additional bag 12 for receiving a flushing solution. Items which correspond to one another have once again been given the same reference numerals. The bag 2 for receiving the adsorbent and the bag 12 for receiving the flushing solution take the form of a two-chambered bag 13, the chamber 2" for the adsorbent and the chamber 12" for the flushing solution being separated from one another by a transversely extending weld 14. The chamber 12" for the flushing solution has an inlet 12A to which a flexible line 12B is connected and which is closed off by a shut-off device 12C. The flexible line 12B runs to a reservoir (not shown) for a flushing solution. The shut-off device 12C having been opened, the chamber 12" can be filled with flushing solution. The shut-off device 12C is then closed again.

The embodiment shown in FIG. 5 is operated in the same way as the embodiment shown in FIG. 1. However, the embodiment shown in FIG. 5 allows the emptied chamber 2" for the adsorbent to be flushed with the flushing solution contained in the chamber 12". For this purpose, the chamber 2" having been emptied, the flushing solution is transferred from the chamber 13" into the chamber 2". This can be done by making a connection for fluid between the chamber 12" and the chamber 2". Situated in the weld 14 there is preferably a passage which is closed off by a fracturable part 15 but which can be opened by fracturing the fracturable part. An alternative embodiment makes provision for the weld 14 between the chambers 2" and 12" to be able to be torn to open it. Multi-chambered bags in which a connection for fluid can be made retrospectively between the individual chambers are generally familiar to the person skilled in the art and because of this there will not be any further description of the two-chambered bag.

The chamber 2" having been flushed with the flushing solution, the flushing solution is transferred into the adsorber housing 1A together with the remainder of the adsorbent. Only then shut-off device 5A is closed. The flexible lines 5, 6, 7 are then once again welded off from the adsorber housing 1A in a sterile manner.

In an alternative embodiment the chamber 2" is not filled with an adsorbent in the form of a suspension. In this embodiment, the chamber 2" is already filled with an adsorbent in powder form which, after the flushing solution has been transferred from the chamber 12" into the chamber 2", is then transferred into the adsorber housing 1A in dissolved form.

Figure 6:
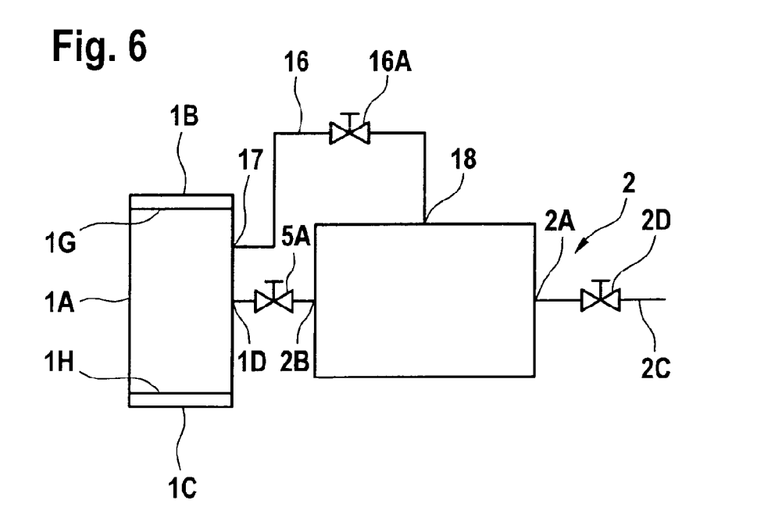
FIG. 6 shows an embodiment of arrangement according to the present invention, in which air situated in the adsorber housing is transferred into the bag for receiving the adsorbent.

The embodiment shown in FIG. 6 differs from the embodiment shown in FIG. 1 in that separate bags are not provided for receiving air and/or fluid. Items which correspond to one another have once again been given the same reference numerals. In the embodiment shown in FIG. 6, the air and/or liquid/fluid situated in the adsorber housing 1A is transferred into the emptied bag 2 which previously held the adsorbent. Provided for this purpose is a flexible line 16 which connects a venting opening 17 in the adsorber housing 1A to a second inlet opening 18 of the bag 2. The flexible line 16 is closed off by a shut-off device 16A. When the bag 2 is being filled, the shut-off device 16A is closed. The shut-off device 16A is opened together with the shut-off device 5A and the adsorbent is transferred from the bag 2 into the adsorber housing 1A. While the adsorbent is flowing from the bag 2 into the adsorber housing 1A, the air and/or liquid/fluid which is displaced in the adsorber housing flows via the flexible line 16A into the volume of space which becomes free in the bag 2.

For an effective sterilization, the intensity of the radiation should amount at all points to at least approx. 25 kGy, so that the intensity of the radiation of approx. 25 kGy ideally represents the minimum intensity at the surface. From a radiation intensity of 50 kGy, considerable damage occurs, which brings about extensive destruction of the activity of the adsorber material. The intensity of the radiation should not exceed 50 kGy in any layer depth of the material. From a radiation intensity of over 35 kGy, damage to the adsorber material reducing the bonding capacity already occurs. The intensity of the radiation, therefore, should preferably not exceed a value of 35 kGy in the material.

Bags with external dimensions of 300×260 mm were irradiated in tests, wherein the filling height of the bags always amounted to less than 15 mm. On average, the layer thickness of the irradiated product stood at approx. 12 mm. The intensity of the radiation amounted to 27 and 28 kGy. The following values were measured at the surface of the product and beneath the product:

| Intensity of radiation [kGy] | Surface intensity [kGy] | Intensity beneath product [kGy] |
| --- | --- | --- |
| 27.0 | 27.1 | 27.9 |
| 28.0 | 29.2 | 31.5 |
| 27.0 | 26.8 | 28.2 |
| 27.0 | 28.0 | 31.9 |
| 27.0 | 27.4 | 29.9 |
| 28.0 | 29.2 | 31.0 |
| 27.0 | 27.7 | 29.3 |

It can be seen that the intensity of the radiation inside the thin layer scarcely changes. The differences compared to the inventive arrangement with the bag, in which the product is distributed in a thin layer, become clear from the following comparative test.

An adsorber column filled wet with adsorber material, having external dimensions of 390×190×90 mm (height=90 mm), a mass of 358 g and a density of 0.054 g/cm$^3$ together with a packing, was irradiated with electrons with an energy of 10 MeV from above and below with a surface intensity on the packing of 24.6 kGy, wherein the intensity of the radiation on the absorber column was measured in the region of the upper side of the column, in the region of the lower side of the column and beneath the column. An intensity of 41.8 kGy was measured on the column and an intensity of 40.5 kGy was measured beneath the column, whilst 51.5 kGy was measured in the column at the top, 58.7 kGy in the middle of the column and 57.2 kGy at the bottom in the column. It can be seen that the minimum in the product amounted to 40.5 kGy and that the maximum lay at 58.7 kGy. The max/min ratio accordingly amounts to 58.7/40.5=1.45. In a second measurement, an intensity of 43.2 kGy was measured on the column and an intensity of 40.6 kGy was measured beneath the column, whilst 55.9 kGy was measured in the column at the top, 57.9 kGy in the middle of the column and 60.3 kGy at the bottom in the column. The max/min ratio accordingly amounts to 60.3/40.6=1.49. Compared to the bag according to the present invention, a relatively marked change in the intensity of the radiation inside the layer can be seen.

The invention claimed is:

1. A method of sterilizing a material which is to be made available in a container, the method comprising:
    filling a sterilization container with the material to be sterilized, the sterilization container being sized such that the material to be sterilized distributes itself in the sterilization container in a thin film or layer,
    irradiating (i) the container in which the material is to be made available and (ii) the sterilization container with high-energy radiation to sterilize the material in the sterilization container, and transferring the material into the container in which the material is to be made available, the sterilization container and the container in which the material is to be made available forming a closed system.

2. The method according to claim 1, wherein the material is a medication.

3. The method according to claim 2, wherein the medication is a medication for infusion or a nutrient.

4. The method according to claim 1, wherein the material to be sterilized is an adsorbent and the container in which the material is to be made available includes an adsorber housing configured to be filled with the adsorbent.

5. The method according to claim 4, wherein the sterilization container is a bag.

6. The method according to claim 4, wherein the adsorbent is transferred into the adsorber housing via a line which connects the sterilization container to the adsorber housing, the line being closed off after the transfer of the adsorbent.

7. The method according to claim 4, wherein at least one of air or excess liquid/fluid situated in the adsorber housing is fed out of the adsorber housing.

8. The method according to claim 7, wherein at least one of air or excess liquid/fluid disposed in the adsorber housing is transferred into a container connected to the adsorber housing via a line.

9. The method according to claim 8, wherein the container for receiving at least one of air or liquid/fluid is a bag.

10. The method according to claim 4, wherein the sterilization container is filled with a liquid/fluid adsorbent.

11. The method according to claim 4, wherein the sterilization container is filled with an adsorbent in powder form.

12. The method according to claim 11, wherein a liquid/fluid is transferred into the sterilization container.

13. The method according to claim 10, wherein a flushing liquid/fluid is transferred into the sterilization container once the adsorbent has been transferred into the adsorber housing, and after the sterilization container has been flushed, the flushing liquid/fluid is transferred into the adsorber housing.

* * * * *